United States Patent
Brown et al.

(10) Patent No.: US 7,744,750 B2
(45) Date of Patent: Jun. 29, 2010

(54) PROCESS FOR REDUCING BROMINE INDEX OF HYDROCARBON FEEDSTOCKS

(75) Inventors: Stephen H. Brown, Bernardsville, NJ (US); James R. Waldecker, Farmington Hills, MI (US); Khavinet Lourvanij, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 391 days.

(21) Appl. No.: 11/282,002

(22) Filed: Nov. 17, 2005

(65) Prior Publication Data

US 2007/0112240 A1    May 17, 2007

(51) Int. Cl.
*C07C 5/08* (2006.01)
(52) U.S. Cl. .............. 208/299; 208/295; 208/307; 208/263; 585/323; 585/643; 585/824; 585/267; 585/249; 585/260; 585/264; 585/273; 585/805
(58) Field of Classification Search .......... 585/267, 585/259, 258, 260, 264, 273, 804, 805; 208/299, 208/301, 307
See application file for complete search history.

(56) References Cited

U.S. PATENT DOCUMENTS

| | | | |
|---|---|---|---|
| 4,104,318 A * | 8/1978 | Hupp et al. ............ 585/319 |
| 4,439,409 A | 3/1984 | Puppe et al. | |
| 4,665,256 A | 5/1987 | Dianis et al. | |
| 4,727,209 A | 2/1988 | Chao | |
| 4,774,379 A | 9/1988 | Butler et al. | |
| 4,795,550 A | 1/1989 | Sachtler et al. | |
| 4,826,667 A | 5/1989 | Zones et al. | |
| 4,849,570 A | 7/1989 | Bakas et al. | |
| 4,891,458 A | 1/1990 | Innes et al. | |
| 4,962,256 A * | 10/1990 | Le et al. ............... 585/467 |
| 5,081,323 A | 1/1992 | Innes et al. | |
| 5,118,896 A | 6/1992 | Steigelmann et al. | |
| 5,146,026 A | 9/1992 | Berna Tejero et al. | |
| 5,149,894 A | 9/1992 | Holtermann et al. | |
| 5,157,158 A | 10/1992 | Berna Tejero et al. | |
| 5,300,722 A * | 4/1994 | Steigelmann et al. ....... 585/467 |
| 5,516,954 A * | 5/1996 | Chang et al. .............. 585/467 |
| 5,877,370 A | 3/1999 | Gajda | |
| 5,955,641 A | 9/1999 | Chen et al. | |
| 5,959,168 A * | 9/1999 | van der Aalst et al. ...... 585/323 |
| 6,005,154 A | 12/1999 | Zones et al. | |
| 6,031,114 A | 2/2000 | DeVries et al. | |

(Continued)

FOREIGN PATENT DOCUMENTS

AU    9856403 A    9/1999

(Continued)

OTHER PUBLICATIONS

U.S. Appl. No. 11/140,182, filed May 27, 2005, Brown et al.

(Continued)

*Primary Examiner*—Tam M Nguyen
(74) *Attorney, Agent, or Firm*—Andrew B. Griffis

(57) ABSTRACT

This invention relates to a process for reducing the Bromine Index of a hydrocarbon feedstock having less than 5 wppm oxygenates-oxygen, comprising the step of contacting the feedstock with a catalyst at conversion conditions to form a first effluent, wherein the catalyst includes a molecular sieve having a zeolite structure type of MWW.

16 Claims, 1 Drawing Sheet

U.S. PATENT DOCUMENTS

| | | |
|---|---|---|
| 6,080,382 A | 6/2000 | Lee et al. |
| 6,096,935 A | 8/2000 | Schulz et al. |
| 6,103,215 A | 8/2000 | Zones et al. |
| 6,111,158 A | 8/2000 | Marinangeli et al. |
| 6,133,497 A | 10/2000 | Hähn et al. |
| 6,297,417 B1 * | 10/2001 | Samson et al. ............... 585/448 |
| 6,323,381 B1 | 11/2001 | Nacamuli et al. |
| 6,368,496 B1 | 4/2002 | Brown et al. |
| 6,500,996 B1 | 12/2002 | Brown et al. |
| 6,525,234 B1 * | 2/2003 | Dandekar et al. ........... 585/467 |
| 6,781,023 B2 | 8/2004 | Brown et al. |
| 7,176,340 B2 * | 2/2007 | Van Broekhoven et al. . 585/449 |
| 7,214,840 B2 * | 5/2007 | Lo et al. ..................... 585/323 |

FOREIGN PATENT DOCUMENTS

| | | |
|---|---|---|
| CZ | 252248 B1 | 8/1987 |
| EP | 0 231 860 | 9/1993 |
| EP | 0 780 458 | 6/1997 |
| EP | 0 704 416 | 1/2000 |
| EP | 0 776 876 | 6/2000 |
| EP | 0 748 305 | 8/2000 |
| EP | 0 952 962 | 10/2001 |
| EP | 0 895 976 | 10/2003 |
| GB | 2279661 | 1/1994 |
| JP | 4198139 A | 7/1992 |
| JP | 4253925 A | 9/1992 |
| WO | 2004/056729 | 7/2004 |

OTHER PUBLICATIONS

"Handbook of Petroleum Processing", McGraw-Hill, New York 1996, pp. 4.3-4.26.

Bailey, G.C. "*Olefin Disproportionation*" Catalysis Reviews, 1970, vol. 3, pp. 44-60.

* cited by examiner

PROCESS FOR REDUCING BROMINE INDEX OF HYDROCARBON FEEDSTOCKS

FIELD

The present invention relates to a process for reducing the Bromine Index (hereafter BI) of hydrocarbon feedstocks such as aromatic hydrocarbon feedstocks. In particular, the present invention relates to a process for reducing the Bromine Index of an extracted feedstock having less than 5 wppm oxygenates-oxygen, comprising the step of contacting the feedstock with a catalyst at conversion conditions, wherein the catalyst includes a molecular sieve having a zeolite structure type of MWW.

BACKGROUND OF INVENTION

Hydrocarbon feedstocks such as aromatic hydrocarbon feedstocks are derived from processes such as naphtha reforming and thermal cracking (pyrolysis). Such feedstocks can be used in a variety of petrochemical processes, such as para-xylene production from an aromatic hydrocarbon feedstock containing benzene, toluene and xylene (BTX), toluene disproportionation, xylene isomerization, alkylation and transalkylation. However, aromatic hydrocarbon feedstocks often contain contaminants comprising bromine-reactive compounds including unsaturated hydrocarbons, such as mono-olefins, multi-olefins and styrenes. These can cause undesirable side reactions in downstream processes. Therefore, these contaminants should be removed from the aromatic hydrocarbon feedstocks before they can be used in other processes.

Improved processes for aromatics production, such as that described in the Handbook of Petroleum Processing, McGraw-Hill, New York 1996, pp. 4.3-4.26, provide increased aromatics yield but also increase the amount of contaminants. For example, the shift from high-pressure semi-regenerative reformers to low-pressure moving bed reformers results in a substantial increase in BI in the reformate streams. These streams are aromatic hydrocarbon feedstocks for downstream processes. This results in a greater need for more efficient and less expensive methods for removal of hydrocarbon contaminants from aromatic hydrocarbon feedstocks, e.g., reformate streams.

Olefins (mono-olefins and multi-olefins) in aromatic hydrocarbon feedstocks are commercially removed by hydrotreating processes. Commercial hydrotreating catalysts have proved active and stable to substantially convert multi-olefins contained therein to oligomers and to partially convert the olefins to alkylaromatics.

The term "mono-olefins" as used herein means olefinic compounds containing one carbon-carbon double bond per molecule. Examples of mono-olefins are ethylene, propylene, butenes, hexenes, styrene, and octenes. The term "multi-olefins" used herein means olefinic compounds containing at least two carbon-carbon double bonds per molecule. Examples of multi-olefins are butadienes, cyclopentadienes, and isoprenes.

The clay treatment of hydrocarbons is widely practiced in the petroleum and petrochemical industries. Clay catalysts are used to remove impurities from hydrocarbon feedstocks in a wide variety of processes. One of the most common reasons for treating these hydrocarbon feedstocks with a clay catalyst system is to remove undesirable olefins, including both multi-olefins and mono-olefins, in order to meet various quality specifications. As used herein the term "olefinic compound" or "olefinic material" is intended to refer to both mono-olefins and multi-olefins. Olefinic compounds may be objectionable in aromatic hydrocarbons at even very low concentrations of less than a few weight parts per million (wppm) for some processes such as nitration of benzene.

More recently, molecular sieves, and particularly zeolites, have been proposed as replacements for clays in the removal of olefinic compounds from aromatic hydrocarbon feedstocks. U.S. Pat. No. 6,368,496 (Brown et al.) discloses a method for removing bromine reactive hydrocarbon contaminants from aromatic streams by first providing an aromatic feedstream having a negligible diene level. The feedstream is contacted with an acid active catalyst composition under conditions sufficient to remove mono-olefins. An aromatic stream may be pretreated to remove dienes by contacting the stream with clay, hydrogenation or hydrotreating catalyst under conditions sufficient to substantially remove dienes but not mono-olefins.

U.S. Pat. No. 6,500,996 (Brown et al.) discloses a method for the removal of hydrocarbon contaminants, such as dienes and olefins, from an aromatics reformate by contacting an aromatics reformate stream with a hydrotreating catalyst and/or a molecular sieve. The hydrotreating catalyst substantially converts all dienes to oligomers and partially converts olefins to alkylaromatics. The molecular sieve converts the olefins to alkylaromatics. The process provides an olefin depleted product which can be passed through a clay treater to substantially convert the remaining olefins to alkylaromatics. The hydrotreating catalyst has a metal component of nickel, cobalt, chromium, vanadium, molybdenum, tungsten, nickel-molybdenum, cobalt-nickel-molybdenum, nickel-tungsten, cobalt-molybdenum or nickel-tungsten-titanium, with a nickel molybdenum/alumina catalyst being preferred. The molecular sieve is an intermediate pore size zeolite, preferably MCM-22. The clay treatment can be carried out with any clay suitable for treating hydrocarbons.

Extracted aromatic feedstocks may contain high level of oxygenates and nitrogen components. The oxygenates and/or nitrogen components may deactivate both clay and molecular sieve catalysts, which decreases the catalyst cycle-length.

Clay treaters used for the treatment of aromatic hydrocarbon feedstocks are generally operated as swing-bed units. When the clay is spent, the aromatic hydrocarbon feedstocks are directed to a second reactor containing fresh clay, while the first reactor is emptied and reloaded. A molecular sieve system has the advantage of long cycle-length, relative to the use of clay. The major disadvantage of a molecular sieve system is the high price of the molecular sieve materials.

The cost of clays and/or molecular sieves has created a need for an efficient and cost-effective method for removing contaminants from hydrocarbon feedstocks such as aromatic hydrocarbon feedstocks. The present invention solves this problem by extending cycle-length by advantageously using a hydrocarbon feedstock having less than 5 wppm oxygenates-oxygen.

SUMMARY OF THE INVENTION

In one embodiment, the present invention relates to a process for reducing the Bromine Index of a hydrocarbon feedstock having less than 5 wppm oxygenates-oxygen, comprising the step of contacting the feedstock with a catalyst at conversion conditions to form a first effluent, wherein the catalyst includes a molecular sieve having a zeolite structure type of MWW.

In another embodiment of the present invention, a process for reducing the Bromine Index of a hydrocarbon feedstock, comprising the steps of:

(a) pretreating the feedstock with a material sufficient to reduce oxygenates-oxygen in said feedstock to less than 5 wppm; and
(b) contacting the pretreated feedstock with a catalyst to form a first effluent, wherein the catalyst includes a molecular sieve having a zeolite structure type of MWW.

In yet another embodiment, this invention relates to a process for reducing the Bromine Index of a hydrocarbon feedstock, comprising the steps of:
(a) pretreating the feedstock with a material sufficient to reduce oxygenates-oxygen in said feedstock to less than 5 wppm;
(b) contacting the pretreated feedstock with a catalyst to form a first effluent, wherein the catalyst includes a molecular sieve having a zeolite structure type of MWW; and
(c) recycling at least a portion of the first effluent to step (b).

In another preferred embodiment, this invention relates to a process for reducing the Bromine Index of a hydrocarbon feedstock having less than 5 wppm oxygenates-oxygen, comprising the steps of:
(a) retrofitting an existing clay treater with a catalyst; and
(b) contacting the feedstock with the catalyst at conversion conditions, wherein the catalyst includes a molecular sieve having a zeolite structure type of MWW, wherein the conversion conditions comprise a temperature range from about 150° C. to about 270° C., a pressure range from about 136 kPa-a to about 6996 kPa-a, and a WHSV from about 0.2 $hr^{-1}$ to about 100 $hr^{-1}$, and the feedstock has a flowrate of at least 10 kg per day.

These and other facets of the present invention shall become apparent from the following detailed description, figures, and appended claims.

DETAILED DESCRIPTION OF THE INVENTION

Figure 1:
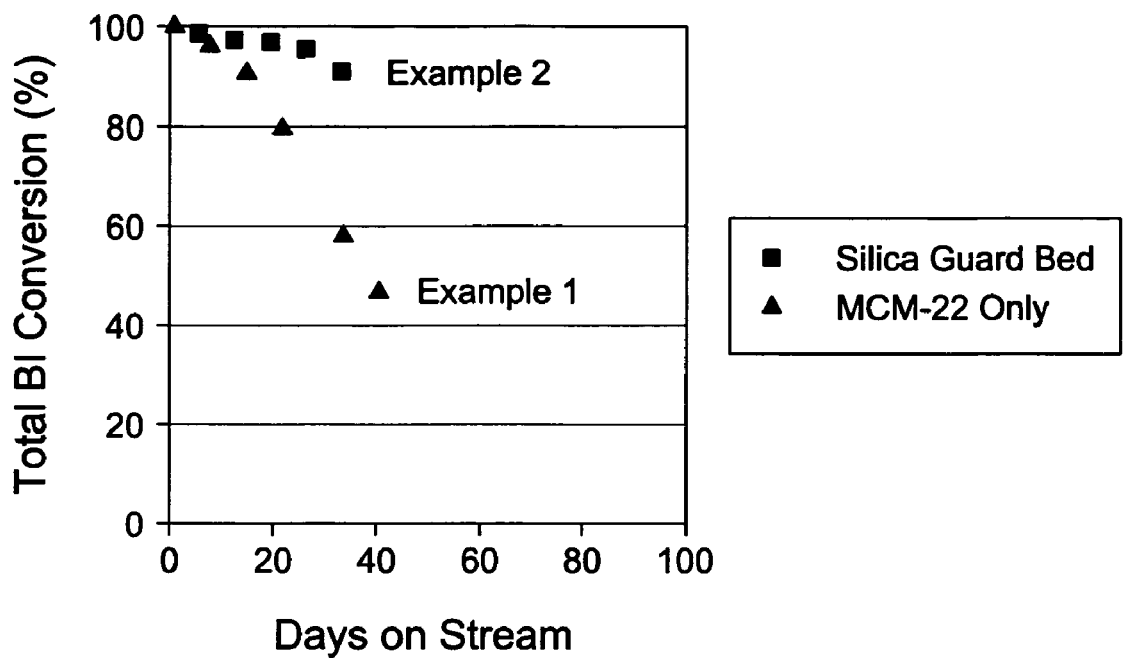
FIG. 1 plots BI conversion versus time on stream for examples 1 and 2.

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The term "on-oil" or "on-stream" as used herein means contacting the feedstock(s) with a catalyst in a reactor e.g., molecular sieve(s), clay(s) or any combination thereof, under conversion conditions. The term "on-oil time" used herein means the time when the catalyst in a reactor is in contact with the feedstock(s) under conversion conditions.

The term "cycle-length" as used herein means the total on-oil time of the clay treater or molecular sieve catalyst before clay/molecular sieve catalyst change-out, rejuvenation, or regeneration. The cycle-length is a function of the hydrocarbon feedstock composition and deactivation rate of the clay/molecular sieve catalyst. In general, high mono-olefinic and/or multi-olefinic compounds and low clay/molecular sieve bed capacity will have a short cycle-length.

The term "feedstock" or "feed" as used herein means the hydrocarbon before contacting the molecular sieve having a zeolite structure type of MWW under conversion conditions. The feedstock or feed may be subjected to chemical processes, such as, distillation, fractionation, adsorption, drying, inert gas purging, or pretreatment processes (e.g., distillation, fractionation, water washing, adsorption, drying, inert gas purging, or catalytic reactions) to remove at least a portion of undesired impurities (e.g., oxygenates, nitrogen compounds, or sulfur compounds).

One important hydrocarbon feedstock is an extracted hydrocarbon feedstock, e.g., extracted aromatic hydrocarbon feedstock. The extraction processes, such as that described in the Handbook of Petroleum Processing, McGraw-Hill, New York 1996, pp. 2.13-2.22, provide a process to recover high purity aromatics from hydrocarbon mixtures, such as reformate.

The hydrocarbon feedstock after extraction may contain some amount of oxygenates (e.g., sulfolane, n-methyl-pyrrolidone, pyrrolidine, dimethyl-sulfoxide, n-formyl-morpholine, morpholine, alcohol, and oxygen) and/or nitrogen components/nitrogen-containing-compounds (e.g., pyridine, n-methyl-pyrrolidone, pyrrolidine, n-formyl-morpholine, and morpholine). The amount of the oxygenates and/or nitrogen components varies from about 0.001 wppm to 10 wt. % depending on the source of the feed, the process of extraction, and separation/purification processes, e.g., distillation. Because there are many varieties of oxygenates and/or nitrogen components, this invention quantifies the amount of oxygenates and/or nitrogen-components with the amount of oxygen contained in the oxygenate and/or the amount of nitrogen contained in the nitrogen-component. The term "oxygenates-oxygen" used herein means the oxygen element contained in the feedstocks, i.e., free oxygen plus oxygen from the oxygenates. The oxygenates-oxygen may be measured by the weight percentage (wt. %) or the weight part per million (wppm) of oxygen element in the feedstocks. The term "nitrogen-compounds-nitrogen" used herein means the nitrogen element contained in the feedstocks, i.e., free nitrogen plus nitrogen from the nitrogen-compounds. The nitrogen-compounds-nitrogen may be measured by the weight percentage (wt. %) or the weight part per million (wppm) of nitrogen element contained in the feedstocks.

The process of the present invention improves the cycle-length by using a hydrocarbon feedstock having less than 1 wt. %, preferably less than 500 wppm, more preferably less than 50 wppm, even more preferably less than 10 wppm, and most preferably less than 5 wppm oxygenates-oxygen. Optionally, the hydrocarbon feedstock of this invention has less than 1 wt. %, preferably less than 500 wppm, more preferably less than 50 wppm, even more preferably less than 1 wppm, and most preferably less than 0.1 wppm nitrogen-components-nitrogen. The process of this invention may further comprise a step of pretreating a hydrocarbon feedstock, such pretreating step is effective to reduce the oxygenates-oxygen in the hydrocarbon feedstock to less than 5 wppm. In one embodiment, the pretreating step may be combined with the contacting step by mixing the pretreating catalyst with the catalyst for BI reduction. While not intending to be limited by any theory, we believe the cycle-length of a catalyst having a molecular sieve can be greatly improved by lowering the oxygenate and/or the nitrogen components because oxygenates and/or nitrogen compounds may deactivate the catalyst or facilitate the deactivation of the catalyst.

Feed

Hydrocarbon feedstocks such as aromatic streams can be obtained from reforming and cracking processes. The hydrocarbon feedstocks include, e.g., paraffins, aromatics, and bromine-reactive compounds such as olefins. For example, aromatic hydrocarbon feedstocks include mononuclear aromatic hydrocarbons and undesirable olefins including mono-olefins, multi-olefins, and styrene, which have an initial BI from about 100 to about 3000.

Because the exact nature of the unsaturated hydrocarbons may vary and may even be unknown, indirect methods of measuring the unsaturated hydrocarbons are typically used. One well-known method of measuring trace amounts of unsaturated hydrocarbons is the BI. The measurement of BI is described in detail in ASTM D2710-92, the entire contents of which are incorporated herein by reference. The BI indirectly measures the olefin content of aromatic containing hydrocarbon samples using potentiometric titration. Specifically, the BI is defined as the number of milligrams of bromine consumed by 100 grams of hydrocarbon sample under given conditions.

The aromatics include, for example, benzene, toluene, xylene, ethylbenzene, cumene and other aromatics derived, e.g., from reformate. Reformate is separated by distillation into light reformate (mostly benzene and toluene), and heavy reformate (including toluene, ortho-, meta- and para-xylenes and other heavier aromatics such as $C_9+$). After extraction, the aromatic feedstream typically contains greater than 98 wt. % aromatics. Heavy reformate feedstocks typically contain less than 0.5 wt. % toluene and less than 250 wppm benzene. Some aromatic streams such as heavy reformate derived from semi-regen and continuous catalyst regeneration (CCR™) reforming processes contain multi-olefins as they emerge from the processing.

The amount of multi-olefins in a hydrocarbon feedstock may vary from less than 10 wt. %, preferably less than 1 wt. %, more preferably less than 500 wppm depending on the source of feedstock and any pre-treatment. Extracted benzenes and heavy reformates typically contain less than 1000 wppm multi-olefins.

The hydrocarbon feedstocks to be processed according to the invention contain bromine-reactive hydrocarbon compounds from about 0.001 to about 10 wt. %, preferably from about 0.001 to about 1.5 wt. %, more preferably from about 0.005 to about 1.5 wt. % or a BI from about 2 to about 20000, preferably from about 2 to about 3000, more preferably from about 10 to about 3000 or most preferably at least 50 to about 3000.

The hydrocarbon feedstock after processing according to the invention will have lower BI than the BI of the hydrocarbon feedstock. In one embodiment the hydrocarbon feedstock processed according to the invention has a BI no greater than 50%, preferably no greater than 20%, more preferably no greater than 10%, of the BI of the hydrocarbon feedstock. In a preferred embodiment, at least a portion of the treated hydrocarbon feedstock recycles to the catalyst bed at the conversion conditions or to another catalyst bed such as a catalyst comprising at least one molecular sieve having a channel size ranging from about 2 Å to 19 Å, a clay, and any combination thereof. Preferably at least 5 wt. %, more preferably at least 10 wt. %, yet more preferably at least 20 wt. %, even more preferably at least 30 wt. %, and most preferably at least 40 wt. % of the treated hydrocarbon feedstock recycles to the catalyst bed at the conversion conditions. Recycling the product back-mixes the product with the feedstock. By recycling a portion of treated hydrocarbon feedstock to the catalyst bed, the diene content in the combined feedstock is lowered because of the low diene content in the treated hydrocarbon stream. The greater the recycle ratio, the closer the reactor approaches operating like a continuous stir tank reactor (CSTR). While not intended to be bound by the theory, we believe that the dienes in the feedstock are more than 10 times more reactive than the olefins. Operating the reactor like a CSTR reduces the concentration of dienes in the feedstock. Reduced diene concentration reduces the probability of reactions between dienes, which are believed to have a higher selectivity for coke. As a result, using recycle can extend catalyst cycle-length. Longer catalyst cycle-length may lower the cost of the catalyst. The hydrocarbon feedstock according to the invention is a hydrocarbon feedstock that preferably has at least 50 wt. % of $C_6$-$C_7$ aromatics, more preferably that has at least 90 wt. % of $C_6$-$C_7$ aromatics, even more preferably that has at least 95 wt. % of $C_6$-$C_7$ aromatics, and most preferably has at least 98 wt. % of benzene plus toluene. In another embodiment, the hydrocarbon feedstock preferably has at least 60 wt. % of benzene, more preferably has at least 90 wt. % of benzene, even more preferably has at least 95 wt. % of benzene, and most preferably has at least 98 wt. % of benzene. In yet another embodiment, the hydrocarbon feedstock preferably has at least 50 wt. % of $C_6$-$C_9$ aromatics, more preferably has at least 90 wt. % of $C_6$-$C_9$ aromatics, even more preferably has at least 95 wt. % of $C_6$-$C_9$ aromatics, and most preferably has at least 98 wt. % of $C_6$-$C_9$ aromatics, wherein the $C_8$ aromatics are ethylbenzene, para-xylene, meta-xylene, and ortho-xylene, the $C_9$ aromatics include cumene, and pseudo-cumene.

In one embodiment, the present invention has a hydrocarbon feedstock flowrate of at least 10 kg per day, preferably more than at least 100 kg per day, more preferably at least 200 kg per day.

Process Conditions

The reaction for catalytically removing bromine-reactive compounds can be any reaction effectively reducing BI. Examples of these reactions are: polymerization of olefinic compounds, alkylation of paraffins and/or aromatics with olefinic compounds, and saturation and/or hydroxylation of the carbon-carbon double bonds of the olefinic compounds in the hydrocarbon feedstocks.

In accordance with the present invention, the above described hydrocarbon feedstocks may be contacted with the molecular sieve(s) and/or clay(s) system under suitable conversion conditions to remove multi-olefins and mono-olefins. Examples of these conversion conditions include a temperature of from about 38° C. to about 538° C., preferably 93° C. to about 371° C., more preferably 150° C. to about 270° C., to a pressure of from about 136 kPa-a to about 6996 kPa-a, preferably from about 205 kPa-a to about 5617 kPa-a, more preferably from about 205 kPa-a to about 3549 kPa-a, a weight hourly space velocity (WHSV) from about 0.1 $hr^{-1}$ and about 200 $hr^{-1}$, preferably from about 0.2 $hr^{-1}$ and about 100 $hr^{-1}$, more preferably from about 2 $hr^{-1}$ and about 50 hr$^{-1}$. The WHSV is based on the total weight of catalyst, i.e., the total weight of active catalyst plus any binder that is used.

In one embodiment, the hydrocarbon feedstock is pretreated with a pretreating catalyst, such as, silica, alumina, silica-alumina, high surface area carbon (e.g., surface area greater than 100 m$^2$/g, preferably greater than 200 m$^2$/g, even more preferably greater than 400 m$^2$/g), molecular sieve, zeolite, or clay to remove the oxygenates and/or the nitrogen components to the desired level. Selective removal of oxygenates and basic nitrogen compounds is typically carried out at near ambient temperature, a pressure from about 136 to about 1480 kPa-a, and WHSV of from about 0.1 to about 5 hr$^{-1}$.

Such pretreatment steps include, but are not limited to, absorption processes in which the hydrocarbon feedstock is contacted with an absorbent under absorption conditions effective to remove at least a portion of such oxygen-containing, nitrogen-containing or even sulfur-containing impurities. Preferably, the absorbent comprises one or more clay materials, including the clay materials previously described herein or an alumina compound (Al$_2$O$_3$), such as Selexsor® CD that may be obtained from Almatis AC, Inc. Preferably, the absorption conditions includes a temperature of from ambient to 500° C., more preferably from ambient to 200° C., or most preferably from ambient to 100° C.; a pressure sufficient to maintain liquid phase conditions; a weight hourly space velocity from 0.5 hr$^{-1}$ to about 100 hr$^{-1}$, more preferably from about 0.5 hr$^{-1}$ to about 10 hr$^{-1}$, most preferably from 1.0 hr$^{-1}$ to 4.0 hr$^{-1}$ depending on the hydrocarbon feedstock being treated. In one embodiment, the pretreating catalyst is located in a separate vessel in front of the vessel packed with the BI reduction catalyst. In another embodiment, the pretreating catalyst is mixed with the BI reduction catalyst or packed on the top of the BI reduction catalyst in the same vessel.

In one embodiment, this invention relates to a process retrofitting existing clay catalyst reactor ("clay treater") with a catalyst comprising at least one molecular sieve catalyst. In a preferred embodiment, this invention relates to a process replacing at least a portion of existing clay catalyst in an existing clay catalyst reactor with a catalyst comprising at least one molecular sieve catalyst. The preferred embodiment abovementioned may further comprise a step of adding a catalyst comprising at least one molecular sieve catalyst to the existing clay treater. In a preferred embodiment, this invention relates to a process replacing at least 10 wt. %, preferably 25 wt. %, more preferably 50 wt. %, most preferably at least 50 wt. %, existing clay catalyst in an existing clay catalyst reactor with a catalyst comprising a molecular sieve catalyst having a zeolite structure of MWW. In yet another preferred embodiment, this invention relates to a process replacing the entire clay catalyst in the existing clay treater with a catalyst comprising at least one molecular sieve catalyst. Another embodiment of this invention comprises a step of adding a catalyst having at least one molecular sieve catalyst to the existing clay treater.

In yet another embodiment, the molecular sieve catalyst and clay catalyst may also be packed in separate reactors. When the molecular sieve catalyst and clay catalyst are in separate reactors, each reactor can have different operating conditions. The molecular sieve catalytic and clay catalytic treating zones may be of any type and configuration that is effective in achieving the desired degree of BI reduction. It may utilize either upward or downward flow, with downward flow being preferred. The pressure in the molecular sieve and clay catalyst system zones should be sufficient to maintain liquid phase conditions. This will normally be a pressure of about 136 kPa-a to about 13891 kPa-a. Preferably the pressure is set about 345 kPa higher than the vapor pressure of the hydrocarbons at the inlet temperature of the molecular sieve/clay zone. This temperature is preferably within the range of from about 132° C. to about 246° C. The molecular sieve and clay catalytic conversion may be performed over a broad range of weight hourly space velocities (WHSV). This variable is often set by the desired on-stream life of the molecular sieve and clay and may range from less than 0.5 hr$^{-1}$ to about 100 hr$^{-1}$, preferably from about 0.5 hr$^-$ to about 10 hr$^{-1}$, more preferably from 1.0 hr$^{-1}$ to 5.0 hr$^{-1}$ depending on the hydrocarbon feedstock being treated.

Catalyst

It is contemplated that any porous particulate materials having a pore size appropriate to catalytically removing bromine-reactive compounds can be employed in this process. The porosity, pore size and pore size distribution in large pores (meso- and macropores) are often of major significance, especially when mass transport affects process performance. The surface properties of the porous particulate material can also be very important for the performance of the material in a given application. The morphology of the porous particulate material (e.g., molecular sieves) can also be another important factor for the performance of the material in this invention. For example, a morphology of small particle size or a morphology of thin layering/plate material can have a large accessible interface. Optionally, the molecular sieve (s) used in this invention has a morphology of small particle size such as an average particle size less than 1 µm, preferably less than 0.1 µm, more preferably less than 0.05 µm or a thin layering/plate morphology having a ratio of the thickness over the average of the other two dimensions less than 0.5, preferably less than 0.1, more preferably less than 0.05, more preferably less than 0.01, more preferably less than 0.005, more preferably less than 0.001.

Microporous particulate materials include crystalline molecular sieves. Molecular sieves are characterized by the fact that they are microporous particulate materials with pores of a well-defined size ranging discretely from about 2 Å to about 20 Å. Most organic molecules, whether in the gas, liquid, or solid phase, have dimensions that fall within this range at room temperature. Selecting a molecular sieve composition with a suitable and discrete pore size therefore allows separation of specific molecules from a mixture with other molecules of a different size through selective adsorption, hence the name "molecular sieve". Apart from the selective adsorption and selective separation of uncharged molecular sieve particles, the well-defined and discrete pore system of a molecular sieve enables selective ion exchange of charged particles and selective catalysis. In the latter two cases, significant properties other than the micropore structure include, for instance, ion exchange capacity, specific surface area and acidity.

A summary of existing technology, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as catalyst supports. A number of long-known techniques, such as spray drying, prilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

Intergrown molecular sieve phases are disordered planar intergrowths of molecular sieve frameworks. These are generally described in the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are periodically ordered in three dimensions. Structurally disordered structures show periodic ordering in dimensions less than three, i.e., in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistic stacking sequences.

The catalyst used in this invention may be an intergrown molecular sieve phases having at least a portion of said intergrown molecular sieve phases comprising a zeolite structure type of MWW. Preferably at least 1 wt. %, more preferably at least 50 wt. %, even more preferably at least 95 wt. %, and most preferably at least 99 wt. % of the intergrown molecular sieve phases comprises a molecular sieve having a zeolite structure type of MWW.

The term "fresh molecular sieve" as used herein means a molecular sieve that has not been exposed for a substantial amount of time (such as 24 hours) to hydrocarbon feedstocks under conversion conditions. Examples of fresh molecular sieve are newly synthesized MCM-22 before or after calcination. The term "spent molecular sieve" used herein, means a non-fresh molecular sieve, i.e., a molecular sieve been exposed for a substantial amount of time (such as 24 hours) to hydrocarbon feedstocks under conversion conditions. Examples of spent molecular sieves are regenerated or rejuvenated MCM-22 after being exposed to a transalkylation feedstock under transalkylation conditions or an alkylation feedstock under alkylation conditions. Typically, a spent molecular sieve has lower catalytic activity than the corresponding fresh molecular sieve.

Molecular sieves/zeolites useful in the present invention include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Structure Types", Eds. W. H. Meier, D. H. Olson and Ch. Baerlocher, Elsevier, Fourth Edition, 1996, the contents of which is hereby incorporated by reference. A large pore zeolite generally has a pore size of at least about 7 Å and includes LTL, VFI, MAZ, MEI, FAU, EMT, OFF, *BEA, MTW, MWW, and MOR structure type zeolites (IUPAC Commission of Zeolite Nomenclature). Examples of large pore zeolites include mazzite, offretite, zeolite L, VPI-5, zeolite Y, zeolite X, omega, Beta, ZSM-3, ZSM-4, ZSM-12, ZSM-18, ZSM-20, SAPO-37, and MCM-22. An intermediate pore size zeolite generally has a pore size from about 5 Å to about 7 Å and includes, for example, MFI, MEL, MTW, EUO, MTT, MFS, AEL, AFO, HEU, FER, and TON structure type zeolites (IUPAC Commission of Zeolite Nomenclature). Examples of intermediate pore size zeolites include ZSM-5, ZSM-11, ZSM-22, ZSM-23, ZSM-34, ZSM-35, ZSM-385, ZSM-48, ZSM-50, ZSM-57, silicalite 1, and silicalite 2. A small pore size zeolite has a pore size from about 3 Å to about 5.0 Å and includes, for example, CHA, ERI, KFI, LEV, SOD, and LTA structure type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, hydroxysodalite, erionite, chabazite, zeolite T, gmelinite, ALPO-17, and clinoptilolite.

The molecular sieve useful for this invention is usually a large pore size zeolite or an intermediate pore size zeolite having a silica-to-alumina molar ratio of at least about 2, specifically from about 2 to 100. The silica to alumina ratio is determined by conventional analysis. This ratio is meant to represent, as closely as possible, the molar ratio in the framework of the molecular sieve and to exclude silicon and aluminum in the binder or in cationic or other form within the channels.

In one embodiment, the molecular sieves for selectively removing mono-olefinic and multi-olefinic compounds include, e.g., large pore zeolites, particularly a molecular sieve having a zeolite structure type of MWW, e.g., MCM-22 (U.S. Pat. No. 4,954,325), MCM-49 (U.S. Pat. No. 5,236,575), MCM-56 (U.S. Pat. No. 5,362,697), and ITQ-1 (U.S. Pat. No. 6,077,498). Preferred catalysts include at one of MCM-22, MCM-49, MCM-56, or ITQ-1. Most preferred are the MCM-22 family of molecular sieves, which includes MCM-22, MCM-49 and MCM-56. The MCM-22 type materials may be considered to contain a similar common layered structure unit. The structure unit is described in U.S. Pat. Nos. 5,371,310, 5,453,554, 5,493,065 and 5,557,024. Each of the patents in this paragraph describing molecular sieve materials is herein incorporated by reference.

In another embodiment, other natural or synthetic crystalline molecular sieves, with ring structures of ten to twelve members or greater, may also be used together with the molecular sieve having a zeolite structure type of MWW. Crystalline molecular sieves useful as catalysts include as non-limiting examples, large pore zeolites ZSM-4 (omega) (U.S. Pat. No. 3,923,639), mordenite, ZSM-18 (U.S. Pat. No. 3,950,496), ZSM-20 (U.S. Pat. No. 3,972,983), zeolite Beta (U.S. Pat. No. 3,308,069 and U.S. Pat. Re No. 28,341), Faujasite X (U.S. Pat. No. 2,882,244), Faujasite Y (U.S. Pat. No. 3,130,007), USY (U.S. Pat. Nos. 3,293,192 and 3,449,070), REY and other forms of X and Y, and mesoporous materials such as M41 S (U.S. Pat. No. 5,102,643) and MCM-41 (U.S. Pat. No. 5,098,684). More preferred molecular sieves include 12 membered oxygen-ring structures ZSM-12, mordenite, Zeolite Beta, USY, layered materials, and mesoporous materials.

Because the catalyst of this invention has longer cycle-length because of lower oxygenates, and/or lower nitrogen components, and optionally, lower dienes in the feed, the catalyst of this invention may operate at more severe conversion conditions, e.g., higher temperature and higher space velocity, than conventional clay catalyst. The catalyst of this invention therefore has even longer cycle-length, wider operating window, and higher throughput potential. As shown in the examples, it is possible to secure at least 2 fold or greater cycle-length improvements through use of the present invention. It is known to those skilled in the art that the advantage of increased cycle-length at constant conditions can often be traded for higher throughput at similar cycle-lengths. Thus the process of the invention provides for debottleneck potentials for existing plants using clay as catalyst for clay treaters. Alternatively, the process of the invention can be used to save on capital costs. The process of the invention can achieve a typical clay cycle-length of 3 to 12 months using as little as 1/10th the weight of conventional acid treated clay. The process of the invention also relieves the environmental burden of current clay systems. Furthermore, the zeolite catalyst of the invention is regenerable and can be used many times.

One measure of the acid activity of a zeolite is the Alpha Value (alpha number). The Alpha Value is an approximate indication of the catalyst acid activity and it gives the relative rate constant (rate of normal hexane conversion per volume of catalyst per unit time). It is based on the activity of the highly active silica-alumina cracking catalyst taken as an Alpha of 1 (Rate Constant=0.16 sec$^{-1}$). The Alpha Value is described in U.S. Pat. No. 3,354,078, in the Journal of Catalysis, Vol. 4, p. 527 (1965); Vol. 6, p. 278, and Vol.; 61, p. 395 (1980), each of which is herein incorporated by reference as to that description. The experimental conditions of the test used include a constant temperature of 538° C., and a variable flow rate as described in the Journal of Catalysis, Vol. 61, p. 395 (1980).

In one embodiment, the molecular sieve(s) has an Alpha Value at least 1, preferably at least 10, more preferably at least 50, even more preferably at least 100, most preferably at least 300.

The crystalline molecular sieve may be used in bound form, that is, composited with a matrix material, including synthetic and naturally occurring substances, such as clay, silica, alumina, zirconia, titania, silica-alumina and other metal oxides. Other porous matrix materials include silica-magnesia, silica-zirconia, silica-thoria, silica-beryllia, silica-titania, as well as ternary compositions such as silica-alumina-thoria, silica-alumina-zirconia, silica-alumina-magnesia, and silica-alumina-zirconia. The catalyst can be used in the form of an extrudate, lobed form (e.g. trilobe), or powder.

The clay catalyst useful for this application is usually an acidic naturally-occurring clay or a synthetic clay material. Naturally-occurring clays include those of the montmorillonite and kaolin families. Clay catalyst system is used herein to refer to the passage of a hydrocarbon stream through a fixed bed of contact material, which possesses the capability of reacting olefinic compounds present in the hydrocarbon stream. Preferably the contact material is an acidic aluminosilicate. It may be either a naturally occurring material, such as bauxite or mordenite clay, or a synthetic material and may comprise alumina, silica, magnesia or zirconia or some other compound, which exhibits similar properties. A preferred clay is F-24 clay produced by Engelhard Corporation. However, several other types of clay are available commercially and are suitable for use in the present invention, including Filtrol 24, Filtrol 25 and Filtrol 62 produced by the Filtrol Corporation, Attapulgus clay and Tonsil clay. In a preferred embodiment, the clays are pretreated with concentrated HCl or $H_2SO_4$ acid.

As previously discussed, clay catalyst system is now conducted over a wide temperature range of from about 93° C. to about 371° C. The conditions utilized in the clay catalyst system are dependent on the hydrocarbon feedstocks and the kind of the clay catalyst used.

Depending on the hydrocarbon feedstock and the operating conditions, two or more separate clay treater vessels can be used on an alternating (i.e., swing) basis to provide continuous operation. A clay reactor can also be used as the swing reactor for the molecular sieve bed when the molecular sieve is being replaced or regenerated.

Surprisingly, the catalyst of the present invention has proved to have high stability and activity. While not wishing to be bound by theory, we believe that lowering the oxygenates and nitrogen components in the feedstock improves dramatically the catalyst lifetime. Optionally, recycling at least a portion of the processed feedstock co-mixing with the fresh feedstock may decrease the amount of dienes in the feedstock which may further extend the catalyst lifetime. The improved BI reduction process can be advantageously operated to a higher end of cycle temperature than conventional processes. The conventional processes typically operate no higher than 210° C. The improved process may be able to operate at temperatures up to 270° C.

The clay has a similar lifetime regardless of the level of trace oxygenates in the feedstock. It is therefore advantageous to lower the oxygenates and nitrogen compounds, optionally the dienes, in the feedstock to be processed by a catalyst having a molecular sieve catalyst.

The molecular sieve and/or clay may be regenerated under regeneration conditions. In one embodiment of the present invention, the molecular sieve and/or clay is regenerated under regenerating conditions comprising a temperature range of about 30 to 900° C., a pressure range of about 10 to 20000 kPa-a, and a WHSV from about 0.1 hr$^{-1}$ to about 1000 hr$^{-1}$, wherein the regenerating conditions comprise a feed having an oxidative reagent such as air, oxygen, and nitrogen oxides.

The molecular sieve and/or clay may be rejuvenated under rejuvenation conditions. In another embodiment of the present invention, the molecular sieve and/or clay is rejuvenated under rejuvenating conditions comprising a temperature range of about 30° C. to about 900° C., a pressure range of about 10 to 20000 kPa-a, and a WHSV from about 0.1 hr$^{-1}$ to about 1000 hr$^{-1}$, wherein the rejuvenating conditions comprise a feed having a reductive reagent, such as hydrogen, $He/H_2$, or $N_2/H_2$.

The following examples illustrate exemplary preferred embodiments.

The EOR BI liter/kg for a catalyst with a feed is the amount of BI converted in liters per kg of catalyst. The EOR BI liter/kg can be calculated by multiplying the space hour velocity, the hours on stream, the average BI conversion, and the average BI in the feedstock divided by the density of the feedstock (kg/liter) as following:

$$EOR\ BI\ \text{liter/kg} = \frac{WHSV \times \text{average } BI \text{ conversion} \times \text{average } BI \text{ in feed} \times TOS}{\text{Density (kg/liter)}}$$

Three hydrocarbon feedstocks having different level of olefinic compounds were used in the following examples. These feedstocks were analyzed using standard gas chromatograph ("GC") analysis and the ASTM BI test (BI). The multi-olefins (mainly dienes) in this invention, were analyzed as follows: 0.50 grams of maleic anhydride (Sigma-Aldrich Corporation, Milwaukee, Wis., USA) was added to in a round bottom flask containing 300 grams of the hydrocarbon feedstock. The flask was equipped with a condenser, placed in a heating mantle, and brought to reflux. After 20 hrs the flask was cooled to room temperature. The entire contents of the flask were concentrated using a rotary evaporator at 75° C. and a pressure below 0.67 kPa-a. A white crystalline product was obtained, weighed, and analyzed by NMR in the manner described by L. B. Alemany and S. H. Brown, Energy and Fuels, 1995, 9:257-268. The NMR showed the product to be largely maleic anhydride/diene adducts. The multi-olefins content of a hydrocarbon feedstock was calculated based on the corresponding multi-olefins weight in the white crystalline product over the total weight of the hydrocarbon feedstock under analysis, i.e., 300 grams. The compositions of these feedstocks are listed in Table 1.

TABLE 1

| Hydrocarbon Feedstock | Feed A | Feed B |
|---|---|---|
| BI | 160-190 | 85-105 |
| Total olefinic compounds (wppm) | 500 | 250 |
| Dienes (wppm) | 200 | Not measured |
| Oxygenates-oxygen (wppm) | 21-206 | less than 1 |
| Total nitrogen components (wppm) | less than 1 | less than 1 |
| Total paraffins (wt. %) | less than 0.5 | less than 0.5 |
| Total aromatics (wt. %) | greater than 97 | greater than 97 |
| Others (wt. %) | less than 1 | less than 1 |

EXAMPLE 1

A MCM-22 catalyst (Si/Al$_2$=25, particle size about 1 mm) was loaded into a fixed-bed reactor. Feed A (Table 1) was pumped through the reactor at 2170 kPa-a, 232° C., and WHSV 40 hr$^{-1}$. The product was sampled and analyzed for the conversion of the bromine reactive molecules in the feedstock (mostly olefins and dienes). Conversion was monitored as a function of time. The results are plotted in FIG. 1.

EXAMPLE 2

The experiment of example 1 was repeated with a bed of dry silica gel placed upstream of the fixed bed reactor. Feed A first passed through the silica gel at WHSV 0.2 hr$^{-1}$ and room temperature before passing across the MCM-22 catalyst. The purpose of the silica gel was to remove trace oxygenates from the feedstock. The results are plotted in FIG. 1.

Analysis of feed A identified the presence of oxygenates including tetraethylene glycol solvent and plasticizers. The tetraethylene glycol was present in a range from about 21 to about 200 wppm. The silica gel is known to be an effective means of selectively removing oxygenates from the feedstock to as low as less than 5 wppm oxygenates-oxygen. As shown in FIG. 1, the examples prove that the stability of the MCM-22 catalyst for the BI reduction is dependent upon the amount of oxygenates in the feedstock. Removing the oxygenates leads to a great improvement in catalyst stability.

EXAMPLE 3

A MCM-22 catalyst (Si/Al$_2$=25, particle size about 1 mm) was loaded into a fixed-bed reactor. Feed B (Table 1) was pumped through the reactor at 2170 kPa-a, 210° C., and WHSV 100 hr$^{-1}$. The product was sampled and analyzed for the conversion of the bromine reactive molecules in the feedstock. Conversion was monitored as a function of time. The results are plotted in FIG. 2. The EOR BI liter/kg for MCM-22 catalyst with feed B is 2.95×10$^6$ BI liter/kg.

EXAMPLE 4

A MCM-22 catalyst (Si/Al$_2$=25, particle size about 1 mm) was loaded into a fixed-bed reactor. Feed A (Table 1) was pumped through the reactor at 2170 kPa-a, 210° C., and WHSV 100 hr$^{-1}$. The product was sampled and analyzed for the conversion of the bromine reactive molecules in the feedstock. Conversion was monitored as a function of time. The results are plotted in FIG. 2. The EOR BI liter/kg for MCM-22 catalyst with feed A is 1.93×10$^6$ BI liter/kg.

Figure 2:
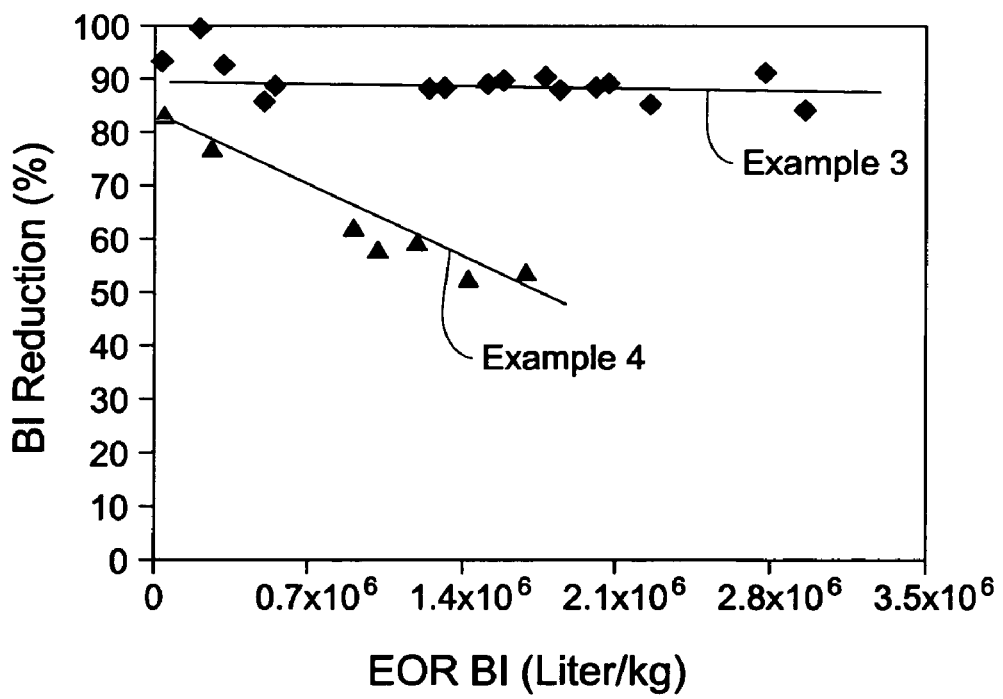
FIG. 2 plots BI reduction versus EOR BI liter/kg for examples 3 and 4.

Feed A has oxygenates-oxygen in a range from about 21 to about 200 wppm. The feed B has oxygenates-oxygen in a range from about 0.1 to 10 wppm. As shown in FIG. 2, the catalyst showed at least 10 fold improvement in stability for feed B versus feed A. The inventors believe that the step-change improvement in performance for the feed B is partly a result of low oxygenates-oxygen levels in feed B.

EXAMPLE 5

A clay catalyst (F-24) was loaded into a fixed-bed reactor. Feed A (Table 1) was pumped through the reactor at 2170 kPa-a, 210° C., and WHSV 2 hr$^{-1}$. The product was sampled and analyzed for the conversion of the bromine reactive molecules in the feedstock. Conversion was monitored as a function of time. The EOR BI liter/kg was 1.05×10$^6$ BI liter/kg.

EXAMPLE 6

A clay catalyst (F-24) was loaded into a fixed-bed reactor. Feed B (Table 1) was pumped through the reactor at 2170 kPa-a, 210°C., and WHSV 2 hr$^{-1}$. The product was sampled and analyzed for the conversion of the bromine reactive molecules in the feedstock. Conversion was monitored as a function of time. The EOR BI liter/kg was 0.38×10$^6$ BI liter/kg.

Comparing examples 3 and 4 with examples 5 and 6, it is clear that the MCM-22 catalyst has much longer catalyst life versus the clay catalyst.

We claim:

1. A process for reducing the Bromine Index of an aromatic hydrocarbon feedstock, comprising the steps of:
   (a) pretreating said feedstock with a catalyst or absorbent to reduce oxygenates-oxygen in said feedstock to less than 5 wppm; and
   (b) contacting said pretreated feedstock with a catalyst to form a first effluent,
   wherein said catalyst in step (b) includes a molecular sieve having a zeolite structure type of MWW;
   then
   (c) passing said first effluent from step (b) to a para-xylene production process.

2. The process according to claim 1, wherein said material of step (a) comprises at least one of silica, alumina, silica-alumina, high surface area carbon, molecular sieve, zeolite, and clay.

3. The process according to claim 1, wherein said feedstock has at least 95 wt. % of C$_6$-C$_7$ aromatics.

4. The process according to claim 1, wherein said feedstock has at least 98 wt. % of benzene.

5. The process according to claim 1, wherein said molecular sieve having a zeolite structure type of MWW comprises at least one of MCM-22, MCM-49, MCM-56, and ITQ-1.

6. The process according to claim 1, wherein said molecular sieve comprises a spent molecular sieve.

7. The process according to claim 1, wherein said catalyst further comprises a clay.

8. The process according to claim 1, wherein said feedstock has a Bromine Index of at least 5.

9. The process according to claim 1, further comprising a step of recycling at least a portion of said first effluent to step (b).

10. The process according to claim 1, further comprising a step of recycling at least a portion of said first effluent to step (a).

11. The process according to claim 1, wherein said first effluent has less than 5 wppm of dienes.

12. The process according to claim 1, wherein said conversion conditions comprise a temperature range from about 150° C. to about 270° C., a pressure range from about 136 kPa-a to about 6996 kPa-a, and a WHSV from about 0.2 hr$^{-1}$ to about 100 hr$^{-1}$.

13. The process according to claim 1, further comprising a step of regenerating said catalyst with an oxidative agent under regeneration conditions having a temperature range of about 30 to 900° C., a pressure range of about 10 to 20000 kPa-a, and a WHSV from about 0.1 hr$^{-1}$ to about 1000 hr$^{-}$.

14. The process according to claim 1, further comprising a step of rejuvenating said catalyst with a reductive agent under rejuvenation conditions having a temperature range of about 30 to 900° C., a pressure range of about 10 to 20000 kPa-a, and a WHSV from about 0.1 hr$^{-1}$ to about 1000 hr$^{-1}$.

15. The process according to claim 1, wherein said feedstock has a flowrate of at least 100 kg per day.

16. The process according to claim 1, wherein said first effluent has less than 5 wppm of dienes.

* * * * *